US012597482B2

(12) United States Patent
Tao et al.

(10) Patent No.: US 12,597,482 B2
(45) Date of Patent: Apr. 7, 2026

(54) TECHNIQUES FOR MODELLING AND OPTIMIZING DIALYSIS TOXIN DISPLACER COMPOUNDS

(71) Applicant: Fresenius Medical Care Holdings, Inc., Waltham, MA (US)

(72) Inventors: Xia Tao, West New York, NJ (US); Vaibhav Maheshwari, Jersey City, NJ (US); Peter Kotanko, New York, NY (US); Stephan Thijssen, New York, NY (US); Nadja Grobe, Huntington, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 455 days.

(21) Appl. No.: 18/128,557

(22) Filed: Mar. 30, 2023

(65) Prior Publication Data

US 2023/0238077 A1    Jul. 27, 2023

Related U.S. Application Data

(63) Continuation of application No. 17/162,030, filed on Jan. 29, 2021, now Pat. No. 11,640,846.

(Continued)

(51) Int. Cl.
*G16B 15/30* (2019.01)
*A61M 1/16* (2006.01)
(Continued)

(52) U.S. Cl.
CPC .......... *G16B 15/30* (2019.02); *A61M 1/1613* (2014.02); *A61M 1/1676* (2014.02); *G16B 5/20* (2019.02);
(Continued)

(58) Field of Classification Search
CPC ... A61M 1/1613; A61M 1/1676; G16B 15/30; G16B 5/20; G16C 20/64; G16C 20/30; G16H 20/17; G16H 20/40; G16H 50/50
See application file for complete search history.

(56) References Cited

U.S. PATENT DOCUMENTS

| | | | | |
|---|---|---|---|---|
| 11,471,578 B2 * | 10/2022 | Maheshwari | ......... | G06F 15/167 |
| 11,640,846 B2 * | 5/2023 | Tao | ........................ | G16H 20/40 |
| | | | | 210/646 |

(Continued)

FOREIGN PATENT DOCUMENTS

| | | | | |
|---|---|---|---|---|
| CN | 106133734 A | 11/2016 | | |
| WO | WO-2012109383 A2 * | 8/2012 | .......... | G01N 33/557 |

OTHER PUBLICATIONS

Xue, C. X., et al. "QSAR models for the prediction of binding affinities to human serum albumin using the heuristic method and a support vector machine." Journal of chemical information and computer sciences 44.5 (2004): 1693-1700. (Year: 2004).*

(Continued)

*Primary Examiner* — Jesse P Frumkin
(74) *Attorney, Agent, or Firm* — KDW Firm PLLC

(57)    ABSTRACT

Systems, methods, and/or apparatuses may be operative to perform a dialysis process that includes a displacer infusion process. In one embodiment, a method for determining a displacer compound may include constructing a plurality of target protein quantitative structure-activity relationship (QSAR) models, one for each of the plurality of binding sites, analyzing a set of candidate compounds using the plurality of QSAR models to determine a set of at least one potential compound with an affinity for binding to each of the plurality of binding sites, and selecting at least one displacer compound from the set of at least one potential compound. Other embodiments are described.

20 Claims, 8 Drawing Sheets

Related U.S. Application Data

(60) Provisional application No. 62/967,738, filed on Jan. 30, 2020.

(51) Int. Cl.

| | |
|---|---|
| *G16B 5/20* | (2019.01) |
| *G16C 20/30* | (2019.01) |
| *G16C 20/64* | (2019.01) |
| *G16H 20/17* | (2018.01) |
| *G16H 20/40* | (2018.01) |
| *G16H 50/50* | (2018.01) |

(52) U.S. Cl.
CPC ............. *G16C 20/30* (2019.02); *G16H 20/17* (2018.01); *G16H 20/40* (2018.01); *G16H 50/50* (2018.01); *G16C 20/64* (2019.02)

(56) References Cited

U.S. PATENT DOCUMENTS

| | | | |
|---|---|---|---|
| 2001/0047086 | A1 | 11/2001 | Cramer |
| 2004/0199334 | A1 | 10/2004 | Kovesdi |
| 2007/0043509 | A1* | 2/2007 | Carter ................ G01N 33/6803 703/11 |
| 2010/0096329 | A1 | 4/2010 | Kotanko |
| 2022/0383992 | A1* | 12/2022 | Triendl ................. G06N 3/044 |

OTHER PUBLICATIONS

Deeb, Omar, and Bahram Hemmateenejad. "ANN-QSAR model of drug-binding to human serum albumin." Chemical Biology & Drug Design 70.1 (2007): 19-29. (Year: 2007).*

Ranganarayanan, Preethi, et al. "Identification of glucose-binding pockets in human serum albumin using support vector machine and molecular dynamics simulations." IEEE/ACM Transactions on Computational Biology and Bioinformatics 13.1 (2015): 148-157. (Year: 2015).*

Serra, Angela, et al. "An integrated quantitative structure and mechanism of action-activity relationship model of human serum albumin binding." Journal of cheminformatics 11.1 (2019): 38. (Year: 2019).*

Gini, Giuseppina, et al. "Could deep learning in neural networks improve the QSAR models ?. " SAR and QSAR in Environmental Research 30.9 (2019): 617-642. (Year: 2019).*

* cited by examiner

_100_

TECHNIQUES FOR MODELLING AND OPTIMIZING DIALYSIS TOXIN DISPLACER COMPOUNDS

CROSS-REFERENCE TO RELATED APPLICATION

This application is a Continuation Application of U.S. application Ser. No. 17/162,030, filed on Jan. 29, 2021, which claims priority to U.S. Provisional Patent Application Ser. No. 62/967,738, filed on Jan. 30, 2020, which is incorporated by reference in its entirety as if fully set forth herein.

FIELD

The disclosure generally relates to a dialysis system, including to techniques for removing target substances from the blood of a patient using a displacer compound during dialysis treatment and, more particularly, to processes for modelling, optimizing, and/or otherwise determining displacer compounds to be used for particular patients, target compounds, treatment regimens, and/or the like.

BACKGROUND

Dialysis machines are known for use in the treatment of renal disease. The two principal dialysis methods are hemodialysis (HD) and peritoneal dialysis (PD). Various unwanted substances may be removed from a patient's blood during a dialysis treatment, including waste products (for instance, urea), toxins, and foreign substances (for instance, prescription drug molecules). In contrast to free or unbound substances, dialysis processes may not be able to effectively remove protein-bound substances because only the unbound fraction of the substance may pass through the membrane of a dialyzer. As a result, protein-bound substances typically require longer dialysis times and/or specific treatment methods to be effectively removed from the blood of a patient during a dialysis treatment.

Various techniques have been used to attempt to remove protein-bound toxins. For example, activated charcoal suspended in the dialysate can help maintain the diffusion gradient of protein-bound uremic toxins and increase their removal. However, this method is not selective and is logistically cumbersome. Attempts have been made to address the issue via increasing certain aspects of toxin removal, such as increasing dialysis session times, dialyzer size, dialysate flow rates, the frequency and duration of dialysis, hemofiltration and hemodiafiltration, the pore size or surface area of dialysis membranes, fractionated plasma separation, and increased convection. Such approaches may have a limited potential to increase protein-bound uremic toxin removal, however, they all suffer from one or more major drawbacks, for instance, high costs, cumbersome implementation, potential unwanted side effects, unknown feasibility or clinical applicability, and an inability to implement in dialysis centers or other healthcare facilities on a large scale.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

The present disclosure relates generally to methods, apparatuses, and systems for a displacer determination process operative to determine displacers for performing displacement dialysis processes for removing protein-bound substances from patient blood. A displacer may be used during dialysis treatment to bind to a protein to displace a target substance (i.e., a toxic substance to be removed via the dialysis treatment) from binding with the protein. In some embodiments, a displacer determination process may include determining displacer characteristics, such as displacer-protein binding sites, applicability to dialysis patients, and/or the like. In various embodiments, quantitative structure-activity relationship (QSAR) models may be developed to screen candidates based on the displacer characteristics. The QSAR models may be used to evaluate, among other things, a binding affinity of a candidate to the protein to determine displacers.

In one embodiment, a method for determining a displacer compound may include constructing at least one QSAR model for analyzing candidate compounds for binding to a target protein based on at least one displacer characteristic.

In one embodiment, a method for determining a displacer compound for binding to a target protein having a plurality of binding sites may include constructing a plurality of target protein QSAR models, one for each of the plurality of binding sites, determine a set of result compounds with an affinity for binding to each of the plurality of binding sites, selecting at least one displacer compound from the set of result compounds.

In one embodiment, a method for removing a target substance from patient blood during a dialysis process may include infusing a patient with a displacer configured to displace binding of the target substance with a target protein to increase an amount of free target substance in the patient blood, the displacer determined via a displacer determination process that may include selecting the displacer using at least one QSAR model configured to model a plurality of binding sites of the target protein.

In one embodiment, an apparatus may include a storage device storing instructions and logic coupled to the storage device, the logic, in response to executing the instructions, to construct a plurality of target protein QSAR models, one for each of the plurality of binding sites, determine a set of result compounds with an affinity for binding to each of the plurality of binding sites, selecting at least one displacer compound from the set of result compounds.

In one embodiment, an apparatus may include a storage device storing instructions and logic coupled to the storage device, the logic, in response to executing the instructions, to infusing a patient with a displacer configured to displace binding of the target substance with a target protein to increase an amount of free target substance in the patient blood, the displacer determined via a displacer determination process that may include selecting the displacer using at least one QSAR model configured to model a plurality of binding sites of the target protein.

In various embodiments, the at least one QSAR model may be configured to predict a binding affinity of a displacer for the target protein. In some embodiments, the at least one QSAR model include at least one albumin binding model and at least one plasma protein binding (PPB) model.

In some embodiments, the target protein may include a plurality of binding sites. In various embodiments, the at least one QSAR model may include one model for each of the plurality of binding sites.

In some embodiments, the target protein may include albumin. In various embodiments, the target protein may include albumin, and the plurality of binding sites may include binding site I and binding site II. In some embodiments, the at least one QSAR model may include a binding site I model to predict a binding affinity of a candidate for binding site I of albumin and a binding site II model to predict a binding affinity of a candidate for binding site II of albumin. In some embodiments, displacer compounds determined via the binding site I model may have an indication of binding affinity of Log $K=\log [\% \text{PPB}/(101-\% \text{PPB})]$. In exemplary embodiments, displacer compounds determine via the binding site II model may have an indication of binding affinity of log K.

Displacer determination processes according to some embodiments, and dialysis processes using displacers selected via displacer determination processes, may have multiple technological advantages over conventional techniques. For example, non-limiting technological advantages may include determining displacer compounds with improved accuracy and that may be more effective for patients. In another example, non-limiting technological advantages may include improving patient quality of life and treatment experience by providing more treatment options and reduce disease and treatment complications. In addition, displacer determination processes may be integrated into multiple practical applications, such as providing dialysis treatment recommendations using selected displacers and performing dialysis using selected displacers.

In addition, introduction of a displacer may lead to unwanted side effects (for instance, with ibuprofen, tryptophan, and/or other known displacers). For example, generating free target substances in the blood may cause the amount of substance to increase to unsafe levels. In another example, the amount of displacer in patient blood may need to be controlled, for example, to not reach unsafe or levels or to otherwise affect the patient beyond binding to a target protein. However, selecting displacers according to displacer determination processes according to some embodiments may allow researchers and/or healthcare professionals to determine optimal displacers, for instance, that are safer and/or that may be controlled for better patient outcome (for instance, that do not require as much dosage, and/or the like). In addition, by determining one or more displacers according to some embodiments, displacers may be selected for patient care that are more efficient, less costly, more readily available, have fewer side effects, are non-toxic or less toxic, personalized for a patient, and/or other beneficial qualities as compared with conventional compounds.

Additional technological advantages and practical applications would be known to those of skill in the art in view of the present disclosure.

BRIEF DESCRIPTION OF THE DRAWINGS

By way of example, specific embodiments of the disclosed machine will now be described, with reference to the accompanying drawings, in which.

DETAILED DESCRIPTION

Figure 1:
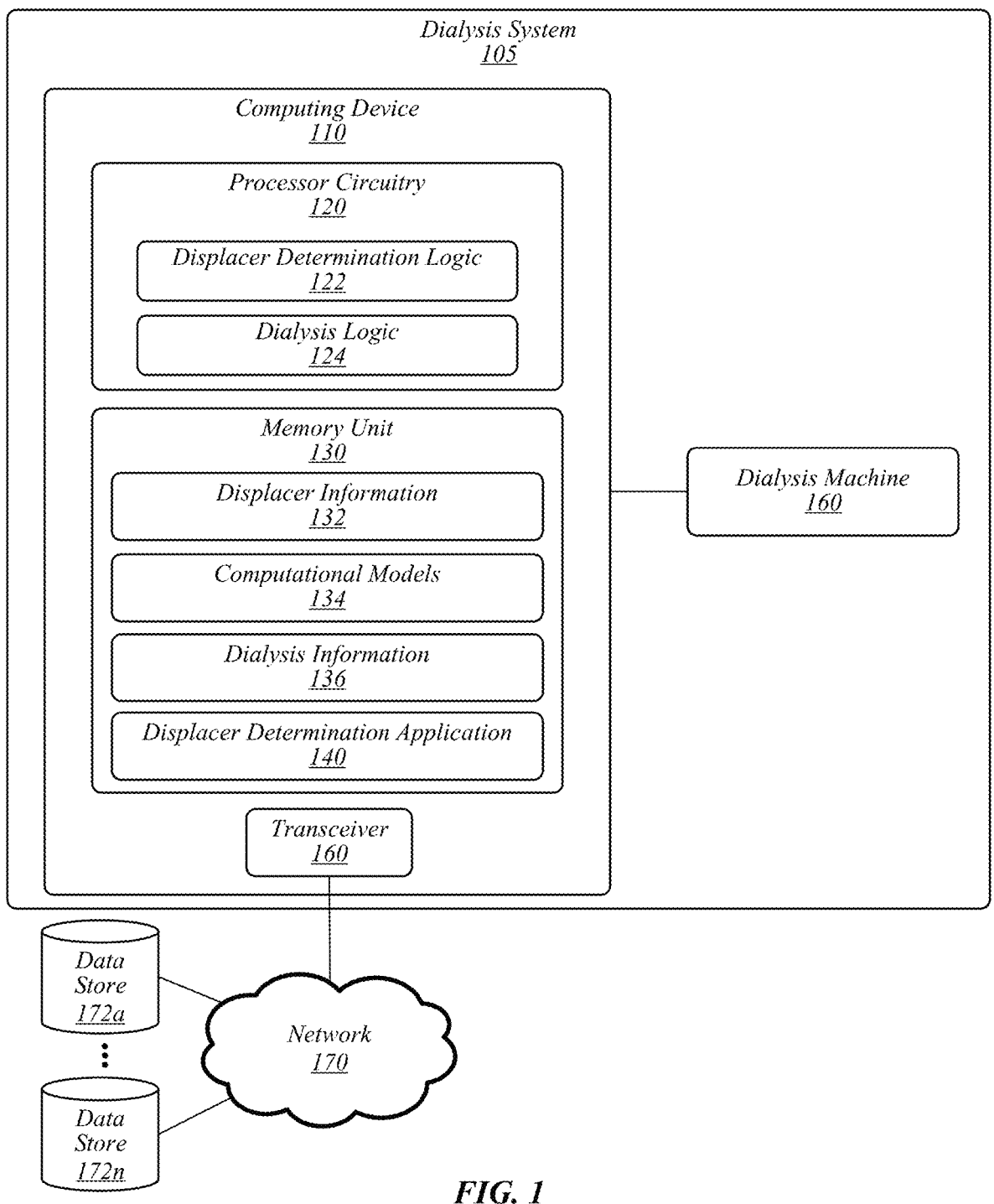
FIG. 1 illustrates an example of a first operating environment that may be representative of some embodiments of the present disclosure.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Various embodiments may generally be directed toward systems, methods, and/or apparatuses for determining displacer compounds that may be used in displacement dialysis processes for removing protein-bound target compounds from patient blood. Non-limiting examples of target compounds may include protein-bound uremic toxins (PBUTs). A displacement dialysis process may introduce a displacer during dialysis treatment that is operative to displace the target substance from the protein in the protein-bound form to generate free substance. In general, a target substance is an unwanted substance for removal via dialysis that may be freed via application of a displacer. A non-limiting example of a displacement dialysis process may include processes the same or similar to methods described in U.S. Pat. No. 8,206,591, titled "Method of Removing Protein-Bound Deleterious Substances During Extracorporeal Renal Replacement Treatment," which is incorporated herein by reference as if fully set forth in the present disclosure.

Generating free target substances in the blood may cause the amount of substance to increase to unsafe levels. In addition, the amount of displacer in patient blood may need to be controlled, for example, to not reach unsafe or levels or to otherwise affect the patient beyond binding to a target protein. Accordingly, displacement dialysis processes according to some embodiments may operate to balance introducing a sufficient amount of the displacer to effectively generate free substance from protein-bound substance for removal via dialysis, while not causing an unsafe level of substance to be present in the blood during the treatment. Accordingly, displacement dialysis processes according to some embodiments may include determining a displacer infusion process or profile operative to manage the infusion of displacer into the blood of a patient during dialysis to facilitate the effective removal of the substance while preventing the substance from reaching an unsafe level. A non-limiting example of a displacement dialysis process using infusion profiles may include processes the same or similar to methods described in U.S. Patent Application Publication No. 2019/0321537, titled "Techniques for Removing Bound Target Substances During Dialysis," which is incorporated herein by reference as if fully set forth in the present disclosure.

Removal of protein-bound uremic toxins (PBUTs) during hemodialysis and convection based hemodiafiltration is difficult. Due to high affinity binding to albumin, only low level of free concentration of PBUTs is available, which results in smaller concentration gradient between blood and dialysate stream, and thus smaller removal. In some embodiments, a method may include infusing the binding competitor(s), which competes with PBUTs for the same binding sites on albumin, into the arterial line of the extracorporeal circuit to increase the free fraction and thus enhance the removal of PUBTs. Essentially, binding competitor augmented hemodialysis is a reactive separation technique and is a paradigm shift from decades old passive-diffusion based hemodialysis. Competitive binding was effective for PBUT removal in ex vivo, in silico, and in an 18 patients' proof-of-concept clinical study. In some embodiments, a mathematic model for optimal infusion profile simulation may be used. In some embodiments, a displacer optimization process may use quantitative structure-activity relationship (QSAR) models with machine-learning methods to screen for better displacers. Some embodiments may use an FDA approved drug database for potential candidate displacers, which can target multiple binding sites on albumin. In some embodiments, a displacer optimization process may identify compounds through the QSAR models for candidate binding competitors and test selected binding competitor(s) in vitro, as well as the effect of their chronic use on pre-dialysis PBUT concentration and patient reported outcomes (PROs)

Uremic toxins have broadly been classified into three categories: (1) Small-sized toxin (<500 Da), (2) middle and large-sized uremic toxins (>500 Da), and (3) protein-bound uremic toxins (PBUTs). Removal of PBUTs is particularly abysmal during conventional hemodialysis (HD). Convection based hemodiafiltration or membrane adsorption could only provide marginal improvement over HD to the removal of this class of toxins. PBUTs removal in the extracorporeal renal replacement therapies is poor because majority of toxin is bound to protein; only a small fraction is available for transfer across dialyzer membrane. Numerous clinical studies suggest that PBUTs exert number of deleterious effects including increased mortality in ESRD patients; enhancing their removal may improve patient outcomes. Although PBUTs, and indoxyl sulfate and p-cresyl sulfate, in particular, are used as examples in this description, embodiments are not so limited as other types of target compounds are contemplated herein.

FIG. 1 illustrates an example of an operating environment 100 that may be representative of some embodiments. As shown in FIG. 1, operating environment 100 may include a dialysis system 105 associated with a dialysis machine 160 (for instance, see dialysis machine 205 of FIG. 2). In various embodiments, dialysis system 105 may include a computing device 110 communicatively coupled to dialysis machine 160. Computing device 110 may be operative to manage, among other things, a displacer determination process according to some embodiments. In various embodiments, computing device 110 may be operative to manage a dialysis process (for instance, a HD process) and/or a displacer infusion process for dialysis machine 160.

Although only one computing device 110 and dialysis machine 160 are depicted in FIG. 1, embodiments are not so limited. In various embodiments, the functions, operations, configurations, data storage functions, applications, logic, and/or the like described with respect to computing device 110 may be performed by and/or stored in one or more other computing devices (not shown), for example, coupled to computing device 110 via network 170. A single computing device 110 and dialysis machine 160 are depicted for illustrative purposes only to simplify the figure. Embodiments are not limited in this context.

Computing device 110 may include a processor circuitry 120 communicatively coupled to a memory unit 130. Processing circuitry 120 may include and/or may access various logics for performing processes according to some embodiments. For instance, processor circuitry 120 may include and/or may access a displacer determination logic 122 and/or a dialysis logic 124. Processing circuitry 120, displacer determination logic 122, and/or dialysis logic 124, and/or portions thereof, may be implemented in hardware, software, or a combination thereof. As used in this application, the terms "logic," "component," "layer," "system," "circuitry," "decoder," "encoder," and/or "module" are intended to refer to a computer-related entity, either hardware, a combination of hardware and software, software, or software in execution, examples of which are provided by exemplary computing architecture 800. For example, a logic, circuitry, or a module may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

Although displacer determination logic 122 and dialysis logic 124 are depicted in FIG. 1 as being within processor circuitry 120, embodiments are not so limited. For example, displacer determination logic 122, dialysis logic 124, and/or any component thereof, may be located within an accelerator, a processor core, an interface, an individual processor die, implemented entirely as a software application (for instance, a displacer determination application 140) and/or the like.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, the memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store a displacer determination application 140 that may operate, alone or in combination with the displacer determination logic 122 and/or the dialysis logic 124 to determine displacer compounds from a pool of candidate compounds. For example, displacer determination application 140 may operate to perform displacer determination processes according to some embodiments. In another example, dialysis logic 124 may operate to perform a dialysis process (for instance, an HD process) via dialysis machine 160.

In some embodiments, memory unit 130 may store displacer information 132. In various embodiments, displacer information 132 may include information associated with potential displacer candidates. For example, displacer information may include a candidate pool from a a compound listing and/or database, such as Food and Drug Administration (FDA) databases, DrugBank (for instance, version 5.1.4), literature-based compound sets (for instance, Zsila et al., "Evaluation of drug—human serum albumin binding interactions with support vector machine aided online automated docking," Bioinformatics 27(13), 1806-1813 (2011) and Zhu et al., "The use of pseudo-equilibrium constant affords improved QSAR models of human plasma protein binding," Pharm. Res. 30(7): p. 1790-8 (2013)), and/or the like.

In some embodiments, displacer information 132 may include displacer requirements, for instance, characteristics or properties of compounds that may be selected as displacer compounds. For example, displacer compounds may be selected as molecules that can be used in the dialysis and end stage renal disease (ESRD) population for the long term. Non-limiting examples of properties for displacer candidates and/or selected displacer compounds may include one or more of: sharing a same binding site (for example, for albumin, sharing an albumin-binding site(s) with most identified target compounds, which is primarily site I and II); having a high affinity that can compete with the albumin binding affinity of PBUTs, or has an approved (e.g., FDA approved) dosage to be administrated in human that will show displacement effects; applicable to a specified delivery process (e.g., are safe and feasible to be administrated intravenously (IV) or through another desired process); do not rely on kidney excretion; and are safe to use with a target patient or patient population (e.g., end stage renal disease population).

In some embodiments, displacer information 132 may include displacer compounds determined via displacer determination processes according to some embodiments. In some embodiments, a dialysis process and/or a healthcare professional may consult displacer information for displacer compounds to be used for a patient as part of a dialysis treatment according to various embodiments.

In some embodiments, computational models 134 may include models used by displacer determination processes to determine displacer compounds. In various embodiments, computational models 134 may be or may include one or more quantitative structure-activity relationship (QSAR) models. In some embodiments, QSAR models may be developed for target proteins (for instance, albumin). In various embodiments, QSAR models may be developed plasma protein binding (PPB). QSAR models according to some embodiments may be constructed to predict binding affinity of candidate compounds for target proteins.

In some embodiments, a target protein may have a plurality of binding sites. For example, a target protein may be albumin, which has two primary binding sites (binding site I and binding site II). QSAR models may be constructed for each binding site. For example, various embodiments may include a binding site I QSAR model and a binding site II QSAR model for albumin. Accordingly, in some embodiments, individual QSAR models may be used to screen candidates for site I and site II binders and obtain their affinity for each site. In some embodiments, for example, QSAR models may be developed for both albumin binding and PPB to predict binding affinity of screened candidates.

In some embodiments, dialysis information 136 may include patient physical information, dialysis treatment or prescription information, target substance information, binding protein information, displacer information, profile determination information, and/or the like. In various embodiments, dialysis information 136 may include a displacer compound to be used or recommended to be used in a dialysis process. In some embodiments, dialysis information 136 may include an infusion profile to be used for a displacer during a dialysis process.

Figure 2:
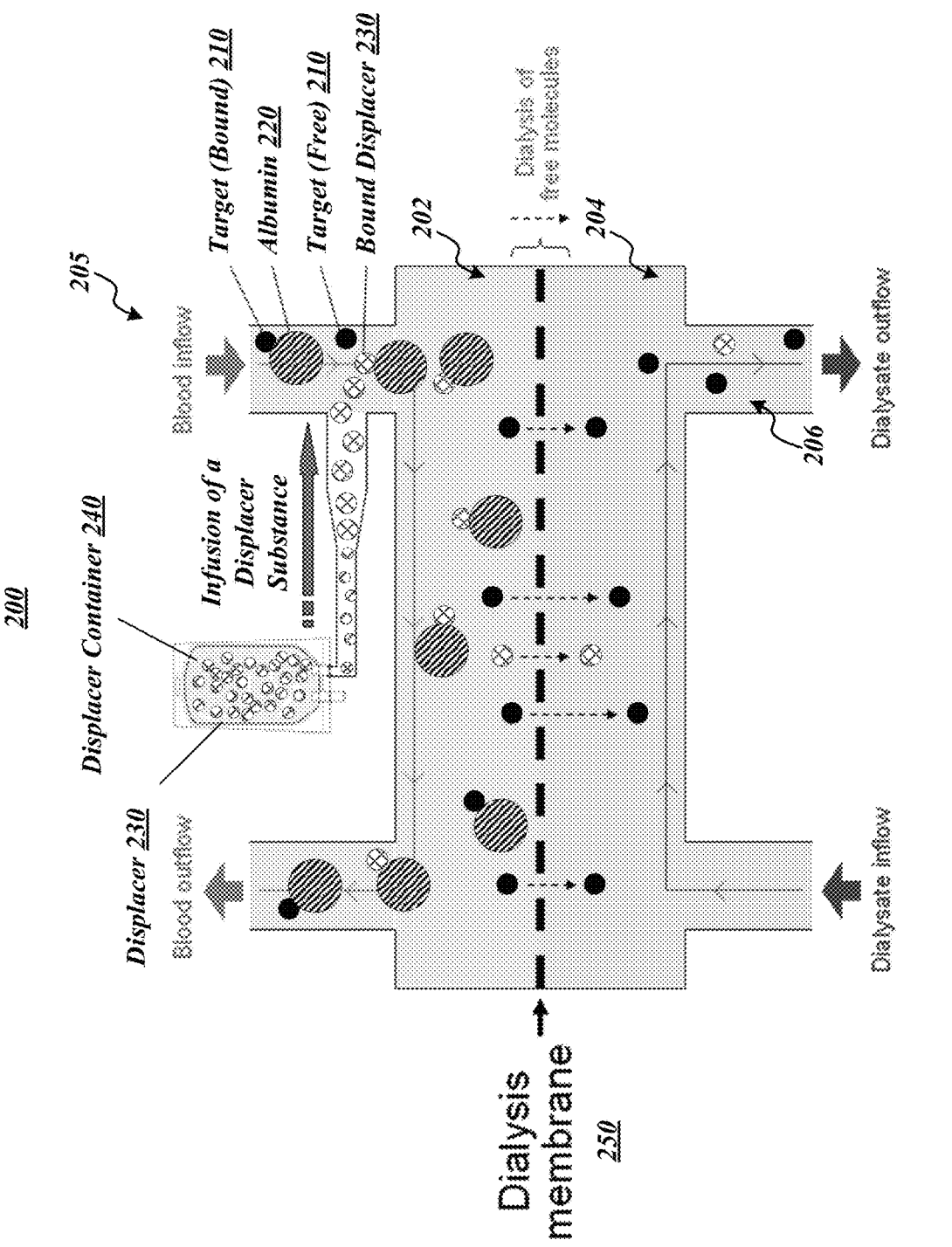
FIG. 2 illustrates an example of a second operating environment that may be representative of some embodiments of the present disclosure.

FIG. 2 illustrates an example of an operating environment 200 that may be representative of some embodiments. Drug-drug interaction is a well-known phenomenon in pharmacokinetics. Compounds that share the same binding site on albumin will interfere with each other's free fraction in plasma which leads to increased or decreased drug action and even causes adverse effects. While drug-drug interactions are usually what clinicians try to avoid, the binding competition mechanism can be borrowed to increase free fraction of PUBTs. By introducing a competitor drug or a combination of few competitors in the extracorporeal circuit blood side pre-dialyzer, higher free fraction of PBUTs might be achieved. Therefore, higher dialytic removal can be expected for PBUTs. This therapeutic method includes may include three components: a displacer or displacer cocktails solution, a programmable infusion pump, and an infusion profile which can be individualized for each patient. Some embodiments may operate to addresses the function area of toxin removal and secretion and the design target number and/or maintain clearance/reduction of small, protein bound uremic toxins (reduction in blood concentration). FIG. 2 depicts competitive binding in a dialysis process according to some embodiments. In general, FIG. 2 depicts a schematic of binding-competition between protein-bound uremic toxin and competitor drug for same binding site. The displacer or competitor drug is infused pre-dialyzer, leading to increase in free toxin concentration, and thus improved dialytic removal.

Figure 7:
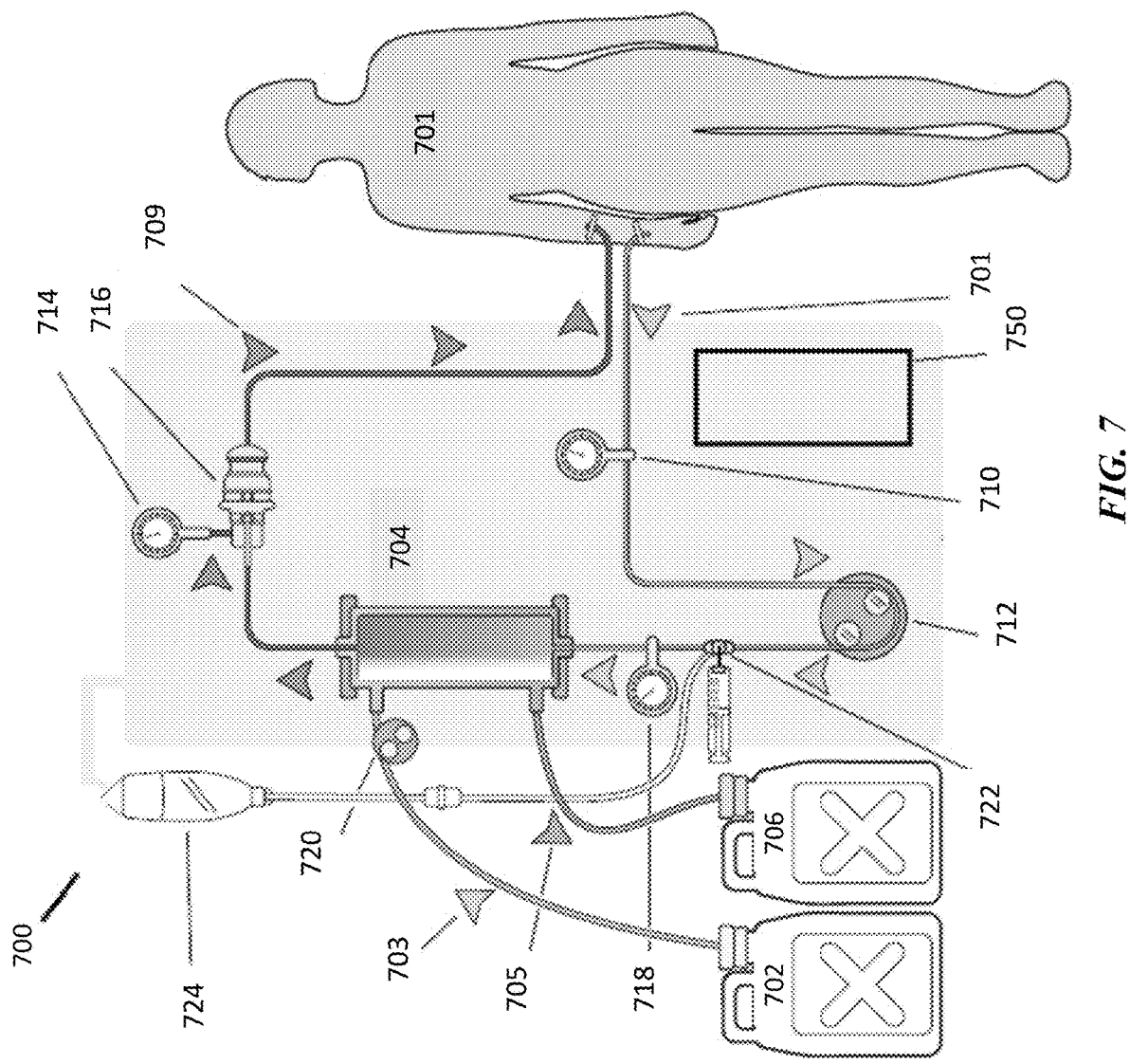
FIG. 7 illustrates an example hemodialysis system.

As shown in FIG. 2, a dialysis machine 205 may operate to cause a dialysate inflow of a dialysis fluid 204 and a dialysis outflow of the dialysate fluid along with unwanted substances 206 (see, for example, FIG. 7). Patient blood 202 may include a target substance (for instance, phenytoin) 210 bound to a target protein (for instance, albumin) 220 and free or unbound target substance 210. Unbound target substance 210 may cross a dialysis membrane 250 and be removed as an unwanted substance 206 with the dialysate outflow. Bound target substance 210 is not able to cross dialysis membrane 250 and, therefore, cannot be removed as an unwanted substance 206 with the dialysate outflow.

In some embodiments, dialysis machine 205 may include or may be in fluid communication with a displacer container 240 operative to facilitate the infusion of a displacer 230 into patient blood 202 via a patient blood inflow. As shown in FIG. 2, displacer 230 may compete for binding sites on albumin 220, leading to a decrease (or even an elimination) of bound target substance 210 and an increase in free target substance 210. An increase in free target substance 210 may facilitate the removal of, or removal of a greater amount of, phenytoin 210 from patient blood 202 than could be achieved in the absence of displacer 230.

In some embodiments, displacer 230 may be selected based on a displacer determination process according to the present disclosure. In various embodiments, displacer 230 may be infused into the patient based on an infusion profile in accordance with the present disclosure.

Figure 3:
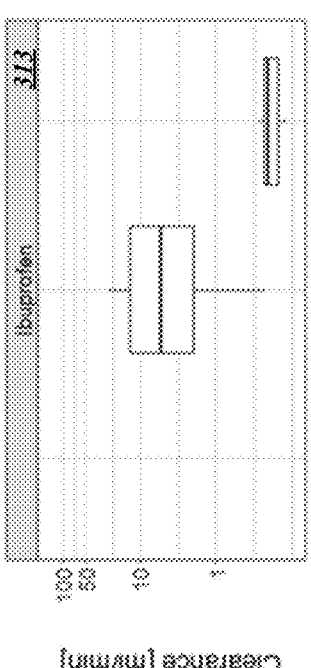
FIG. 3 illustrates exemplary graphs of dialysate clearance of target substances during a plurality of dialysis processes according to the present disclosure.
Figure 3:
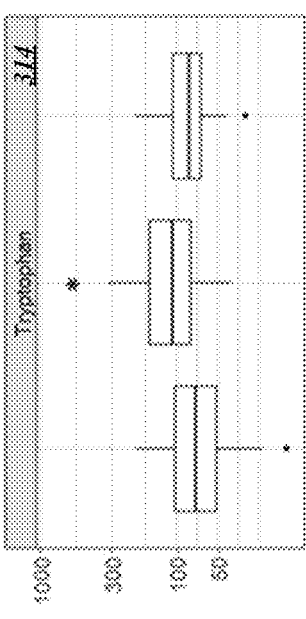
Figure 3:
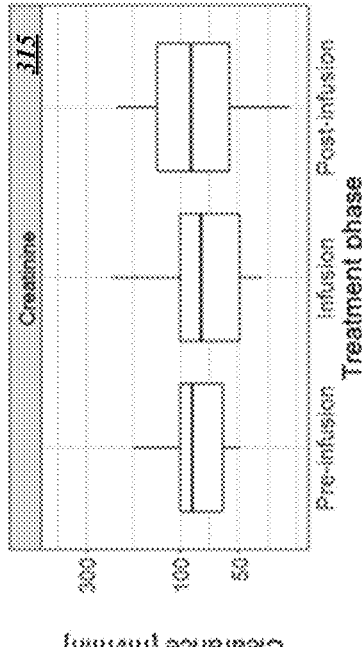
Figure 3:
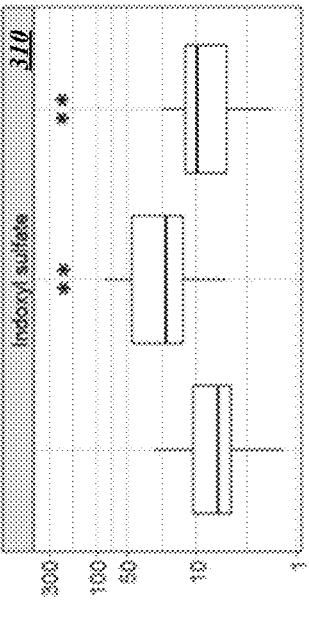
Figure 3:
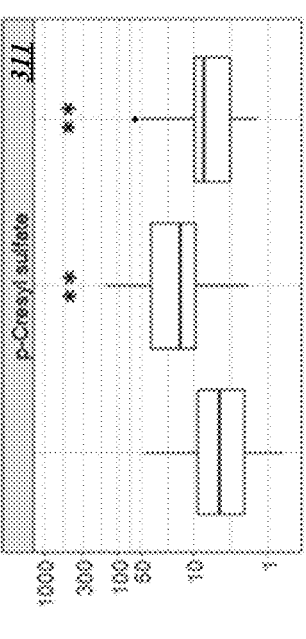
Figure 3:
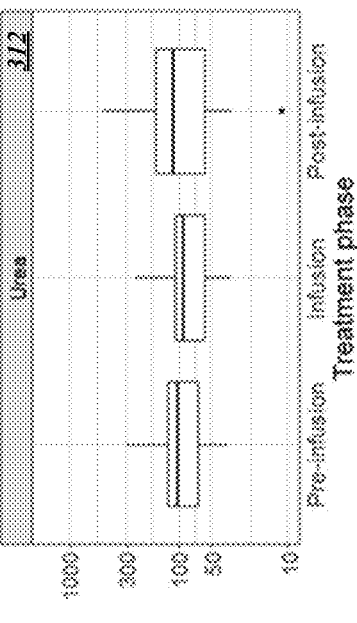

Displacer dialysis methods according to some embodiments have been tested in in vitro, ex vivo, and in at least one clinical study. Among many compounds tested in in vitro studies, ibuprofen has been used as the prototype competitor in a proof-of-concept clinical study with 18 HD patients. For example, ibuprofen (800 mg) was infused from minutes 20 to 40 during routine high-flux hemodialysis. Observations were conducted of the dialysate clearances of indoxyl sulfate (IS) and p-cresyl sulfate (pCS) (both prominent examples of PBUTs) increased from 6.6 to 20 mL/min and 4.4 to 14.9 mL/min, respectively. Infusion of ibuprofen was well tolerated in all patients. FIG. 3 illustrates exemplary graphs of dialysate clearance of target substances during a plurality of dialysis processes according to the present disclosure. In general, graphs 310-315 of FIG. 3 depict information associated with dialytic clearance of different solutes. Between pre-infusion and infusion phase, significant increase in IS and pCS clearance can be observed, but clearance of urea and creatinine (non-protein bound solutes) does not increase.

Figure 4:
FIG. 4 illustrates exemplary graphs of infusion profiles according to some embodiments of the present disclosure.

In some embodiments, one or more mathematical models may be used, for example, that which are calibrated and/or validated by using clinical data. These models may be used to develop infusion profiles to maximize the efficacy of displacer and/or minimize its dosage. The optimized infusion profile may be used to control the infusion pump during treatment. For example, if a displacer is well-tolerated but requires high dosage during HD session due to weak binding affinity, the infusion profile can guide the infusion pump to achieve maximum displacement during HD. On the other hand, minimized residual blood concentration of some displacers can be achieved by improving their efficacy through using infusion profiles according to some embodiments. FIG. 4 illustrates exemplary graphs of infusion profiles according to some embodiments of the present disclosure. In particular, FIG. 4 shows graphs 410-413 of an example infusion profile 410 and simulated concentration of indoxyl sulfate in plasma and interstitial pool 411-413. In some embodiments such infusion profiles may be used to develop and/or control hardware and/or software solutions to program and/or control an infusion pump during a dialysis process according to some embodiments.

Some embodiments may provide displacement determination processes operative to use QSAR modeling. For example, one or more QSAR models may be generated to determine displacers, for instance, compounds that bind to a target protein. A non-limiting example of a target protein may be albumin. In an embodiment with an albumin target protein, a QSAR model may be used to screen compounds for site I and site II binders and obtain their affinity for each site. In some embodiments, QSAR models may be developed for both albumin binding and plasma protein binding (PPB) to predict binding affinity of screened drugs. In one case study, a set of 1240 chemicals were used with known plasma protein binding data literatures (see, for example, Zhu et al.) to build a PPB model. This model may be tested on a set of candidates with known albumin binding data. The binding affinity of tested candidate compounds may be evaluated by both models.

Additional classification QSAR models (for instance, using machine learning (ML) and/or artificial intelligence (AI)) methods may be developed separately for binding site I and binding site II to discriminate the binding site for each compound. The obtained balanced accuracy may be in the range of 86% to 91% for binding site I models and 79% to 88% for binding site II models. Candidates may be accessed from various sources. In one non-limiting example, candidates may include FDA approved drugs with reported intravenous route (IV) of administration (for example, extracted from a DrugBank database). In one example, 169 binding site I binders and 149 drugs site II binders were identified. They were tested against PPB and human serum albumin (HSA) regression QSAR models to estimate binding affinity of these drugs. The results include a list of binding site I and a list of binding site II binders with Log K=log [% PPB/(101−% PPB)] and log K, respectively, as indication for binding affinity. The overlapping of both lists are those compounds which bind to both site I and II.

Solutions according to some embodiments are not limited to improving the mortality of ESRD patients. For example, processes according to some embodiments may improve the patient's quality of life (QoL) by providing more treatment options and reduced disease and treatment complications. For instance, increased p-cresol sulfate is reported to be associated with pruritus severity measured by the 5-D itch scale. Uremic pruritus causes 24% of CKD patients in the US for moderate to severe itching and is associated with decreased patient-reported QoL, more severe depression symptoms and restless sleeping. Hemoperfusion and oral charcoal were tested as treatment options for pruritus. These previous studies suggest that improving the dialytic removal of protein-bound uremic toxins may contribute to reduction of ESRD related complications and thus improve the QoL for patients.

Some embodiments may operate to improve the models to distinguish the primary binding site for each compound, for example, via protein-ligand docking methods, and to predict the site-specific equilibrium constants. In some embodiments, for example, a final list of top displacer candidates may be screened in a laboratory setting to confirm their displacement capabilities to several known PBUTs. Based on the lab results, one or more top candidates may be chosen for a clinical study.

In some embodiments, candidates may be determined based on machine learning ML and/or AI models. In various embodiments, such candidate selection and/or optimization models may take potential deleterious effects into account. For example, like many other blood purification techniques which rely on solute diffusion and convection, the proposed solution may unselectively enhance the removal of toxins and beneficial substances in blood. Models and/or processes according to some embodiments may determine the net benefits of the proposed solution, for example, to determine a balancing point of gain and loss to select an optimal displacer compound. For example, some embodiments may determine whether displacer(s) (alone, or in combination with certain pre-selected infusion profiles) can improve removal of majority of PBUTs without clinically relevant side effects.

Processes according to some embodiments may provide improved clinical outcomes and quick penetration in the current dialysis scenario as the competitive-binding technique is inexpensive and easy to implement with very minor change in current HD technology. For example, the displacer(s) can be infused via a built-in heparin pump, that is frequently not used (many dialysis provider use bolus heparinization instead). A programmable infusion pump for infusion of displacers with an optimized infusion profile is also inexpensive. Such optimal infusion profile(s) can be obtained using mathematical models, patient characteristics, choice of binding-competitor drug, etc. according to some embodiments.

EXAMPLES

QSAR models were developed for both albumin binding and plasma protein binding (PPB) to be used to predict binding affinity of chemicals. A set of 1240 chemicals were used with known plasma protein binding data literatures to build the plasma protein binding model. This model was tested on a set of molecules with known albumin binding data. The results from both plasma binding model and the albumin binding model were compared and no significant difference in performance was found. The binding affinity of a tested compound may be evaluated by both models. The better the agreement between these two models the more realizable the prediction is on a compound.

A next step was to discriminate binding by developing QSAR models separately for binding site 1 (or site I) and binding site 2 (or site II). Classification models ("yes" or no") were developed for these two sites.

Among the set of 1240 chemicals used to build the PPB model, 69 of them were used which has low PPB binding affinity as negative site I binder and a set of 61 positive albumin site I binding chemicals from literatures (for example, Zsila et al.) to train a classification QSAR model. This model was validated by a set of 15 known site I binder from a separate source (for example, Kratochwil et al., "Predicting plasma protein binding of drugs: a new approach," Biochemical Pharmacology, V. 64, Issue 9, pp. 1355-1374 (2002)) and 13 negative site I binders selected from literatures (for instance, Zsila et al.). Six QSAR models were developed with three different molecular descriptors and two machine-learning methods. The obtained balanced accuracy was in the range of 86% to 91%.

Using a similar approach, eight site II binding models with four different molecular descriptors and two machine-learning methods were built. The obtained balanced accuracy was in the range of 89% to 99% for the training set and 79% to 88% for the validation set.

A next step was to apply these QSAR models to select potential site I and II binders separately from an FDA approved drugs database. For example, a drug database was downloaded from the DrugBank website (v 5.1.4). Only FDA approved drugs with intravenous route (IV) of administration route in record were extracted from this database. In total, 514 drugs were tested against two HSA Site1 classification QSAR modes to identify potential binders to HSA Site I and two HSA Site II classification QSAR modes to identify potential binders to HSA Site II. 169 site I binders and 149 drugs site II binders were then identified and tested against PPB and HSA regression QSAR models to identify binding affinity of these drugs. The results include a list of site I binders with Log K=log [% PPB/(101-% PPB)] as indication for binding affinity and a list of site II binders with log K as indication for binding affinity. The overlapping of both lists are those compounds which bind to both site I and II.

Some embodiments may operate to optimize or otherwise improve the models, for example, to distinguish the primary binding site for each compound via protein-ligand docking method and predict the site specific equilibrium constants.

The set was randomly split into training (1019 compounds) and test (113 chemicals) set. Log K=log [% PPB/(101-% PPB)] value was used as input.

After removing duplicated and outliers the final set contained 1132 chemicals. This set was randomly split into training (1019 compounds) and test (113 chemicals) set. Run modeling with different descriptors and built a consensus model (for example, without Chemaxon as this model gives the lowest accuracy). A reasonable correlation was obtained for the developed model, R2=0.75 for training set and R2=0.79 for the test set. This model showed a R2=0.74 and RMSE of 0.46 for predicting the albumin binding for a set of 120 chemicals.

Included herein are one or more logic flows representative of exemplary methodologies for performing novel aspects of the disclosed architecture. While, for purposes of simplicity of explanation, the one or more methodologies herein are shown and described as a series of acts, those skilled in the art will understand and appreciate that the methodologies are not limited by the order of acts. Some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation. Blocks designated with dotted lines may be optional blocks of a logic flow.

A logic flow may be implemented in software, firmware, hardware, or any combination thereof. In software and firmware embodiments, a logic flow may be implemented by computer executable instructions stored on a non-transitory computer readable medium or machine readable medium. The embodiments are not limited in this context.

Figure 5:
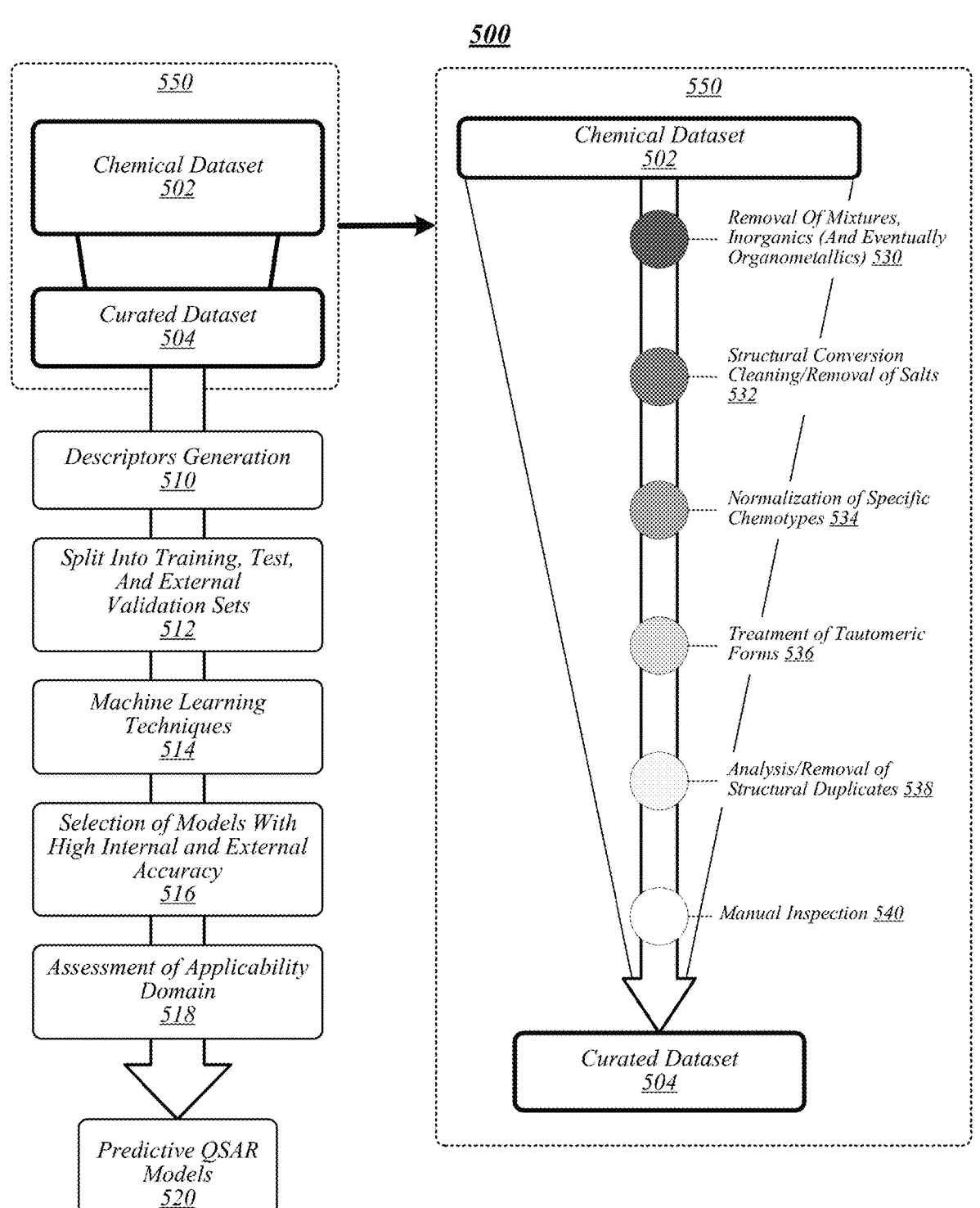
FIG. 5 illustrates a first logic flow in accordance with the present disclosure.

FIG. 5 illustrates an embodiment of a logic flow 500. Logic flow 500 may be representative of some or all of the operations executed by one or more embodiments described herein, such as computing device 110, and/or components thereof. In some embodiments, logic flow 500 may be representative of some or all of the operations of constructing a QSAR model.

Logic flow 500 may determine a curated data set 550. For example, logic flow 500 may access a chemical dataset 502 and perform removal of mixtures and/or inorganics at block 530, perform structural conversion cleaning/removal of salts at block 532, perform normalization of specific chemotypes at block 534, perform treatment of tautomeric forms at block 536, perform analysis/removal of structural duplicates at block 538, and/or perform manual inspection at block 540 to obtain curated dataset 504. In some embodiments, determining a curated data set 550 may be the same or similar to processes described in Fourches et al, "Trust, but verify: On the importance of chemical structure curation in cheminformatics and QSAR modeling research," J. Chem. Inf. Model, 50(7), 1189-1204 (2010).

At block 510, logic flow 500 may perform descriptors generation. Logic flow 500 may proceed to split the dataset into training, test, and/or external validation sets at block 512. At block 514, logic flow 500 may apply machine learning techniques. At block 516, logic flow 500 may select models with a high internal and/or high external accuracy. Logic flow 500 may determine an assessment of an applicability domain at block 518. Logic flow may construct and/or select one or more predictive QSAR models at block 520.

Figure 6:
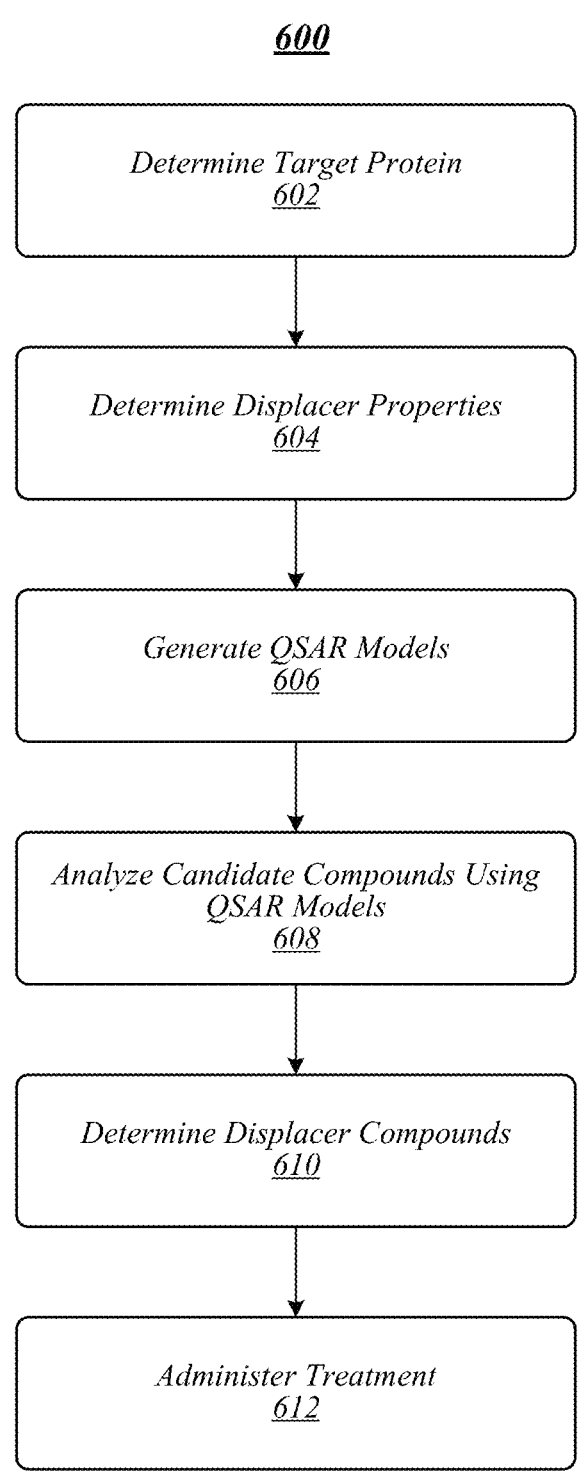
FIG. 6 illustrates a first logic flow in accordance with the present disclosure.

FIG. 6 illustrates an embodiment of a logic flow 600. Logic flow 600 may be representative of some or all of the operations executed by one or more embodiments described herein, such as computing device 110, and/or components thereof. In some embodiments, logic flow 600 may be representative of some or all of the operations of determining a displacer compound via a displacer determination process.

Logic flow 600 may determine a target protein at block 602. For example, a target protein that binds a target compound (for instance, a PBUT) may be determined. A non-limiting example of a target protein may include albumin. At block 604, logic flow 600 may determine displacer properties. In some embodiments, displacer properties may include desired characteristics of a displacer compound. For example, displacer properties may include a binding site (for instance, binds to one or more binding sites of a target protein, binds only to a certain binding site), binding affinity (for instance, has a minimal and/or maximum binding affinity), patient safety properties, solubility, binds to other compounds (for instance, does not bind to certain other compounds in the blood), and/or the like.

Non-limiting examples of properties for displacer candidates and/or selected displacer compounds may include one or more of: sharing a same binding site (for example, for albumin, sharing an albumin-binding site(s) with most identified target compounds, which is primarily site I and II); having a high affinity that can compete with the albumin binding affinity of PBUTs, or has an approved dosage to be administrated in human that will show displacement effects; are safe and feasible to be administrated intravenously (IV); do not rely on kidney excretion; and are safe to use in end stage renal disease population.

At block 606, logic flow 600 may generate QSAR models. In some embodiments, a plurality of QSAR models may be generated. Non-limiting examples of QSAR models may include a target protein QSAR model, a PPB model, and/or one or more models for each potential binding site.

In various embodiments, QSAR models may be developed plasma protein binding (PPB). QSAR models according to some embodiments may be constructed to predict binding affinity of candidate compounds for target proteins.

In some embodiments, a target protein may have a plurality of binding sites. For example, a target protein may be albumin, which has two primary binding sites (binding site I and binding site II). QSAR models may be constructed for each binding site. For example, various embodiments may include a binding site I QSAR model and a binding site II QSAR model for albumin. Accordingly, in some embodiments, individual QSAR models may be used to screen candidates for site I and site II binders and obtain their affinity for each site. In some embodiments, for example, QSAR models may be developed for both albumin binding and PPB to predict binding affinity of screened candidates.

The QSAR models for each binding site, in an example with a target protein of albumin, may operate to discriminate binding by developing QSAR models separately for binding site 1 (or site I) and binding site 2 (or site II). In some embodiments, the QSAR models may operate as classification (i.e., binary or yes/no) models indicating whether or not a candidate is able to bind to a particular binding site. In various embodiments, the QSAR models may operate as quantification models, for instance, indicating a binding affinity (not only yes/no, but classified based on binding affinity values) or other characteristic (e.g., solubility, toxicity, and/or the like).

In some embodiments, for example, a set of K compounds with known binding information may used to build a QSAR model. A portion of K compounds may be known to not bind to the target protein (e.g., negative binding affinity) and a portion of K compounds may be known to bind to the target protein. The known/unknown binding affinity compounds may be used to train and/or validate the QSAR model.

Logic flow 600 may analyze candidate compounds using QSAR models at block 608. For example, a list, set, database, and/or other source of candidate compounds may be analyzed using QSAR models generated according to some embodiments. In various embodiments, output from the QSAR models may indicating a binding affinity for one or more binding sites of the target protein. For example, the results of using QSAR models for binding site I and binding site II may include a list of site I and a list of site II binders with Log K=log [% PPB/(101−% PPB)] and log K, respectively, as indication for binding affinity. The overlapping of both lists are those compounds which bind to both site I and site II.

At block 610, logic flow 600 may determine displacer compounds. For example, selection criteria may be used to select compounds listed based on the analysis performed in block 608. Selection criteria may include availability, toxicity, ability to be integrated into a dialysis process, cost, and/or the like. In some embodiments, compounds determined via the analysis of block 608 may be selected and subjected to experimentation, including in silico, in vivo, ex vivo, and/or clinical trials. Embodiments are not limited in this context.

Logic flow 600 may administer treatment at block 612. In some embodiments, administering treatment may include providing a treatment recommendation to use a determined displacer compound, an infusion profile, and/or the like. In various embodiments, administering treatment may include performing a dialysis treatment using a displacer compound determined using a displacer determination process according to some embodiments. Administering treatment may include computer-assisted, manual (i.e., performed by a healthcare professional), and/or combinations thereof.

FIG. 7 illustrates a diagram of an exemplary embodiment of a dialysis system 700 in accordance with the present disclosure. Dialysis system 700 may be configured to provide hemodialysis (HD) treatment for a patient 701. Fluid reservoir 702 may deliver fresh dialysate to a dialyzer 704 via tubing 703, and reservoir 706 may receive spent dialysate once it has passed through dialyzer 704 via tubing 705. A hemodialysis operation may filter particulates and/or contaminates from a patient's blood through a patient external filtration device, for example, a dialyzer 704. As the dialysate is passed through dialyzer 704, unfiltered patient blood is also passed into dialyzer 704 via tubing 707 and filtered blood is returned to patient 701 via tubing 709. Arterial pressure may be monitored via pressure sensor 710, inflow pressure monitored via sensor 718, and venous pressure monitored via pressure sensor 714. An air trap and detector 716 may ensure that air is not introduced into patient blood as it is filtered and returned to patient 701. The flow of blood and the flow of dialysate may be controlled via respective pumps, including a blood pump 712 and a fluid pump 720. Heparin 722, a blood thinner, may be used in conjunction with saline 724 to ensure blood clots do not form or occlude blood flow through the system.

In some embodiments, dialysis system 700 may include a controller 750, which may be similar to computing device 110 and/or components thereof (for instance, processor circuitry 120). Controller 750 may be configured to monitor fluid pressure readings to identify fluctuations indicative of patient parameters, such as heart rate and/or respiration rate. In some embodiments, a patient heart rate and/or respiration rate may be determinable by the fluid pressure in the fluid flow lines and fluid bags. Controller 750 may also be operatively connected to and/or communicate with additional sensors or sensor systems, devices, and/or the like, although controller 750 may use any of the data available on the patient's biologic functions or other patient parameters. For example, controller 750 may send patient data to computing device 110 to perform processes according to some embodiments.

Figure 8:
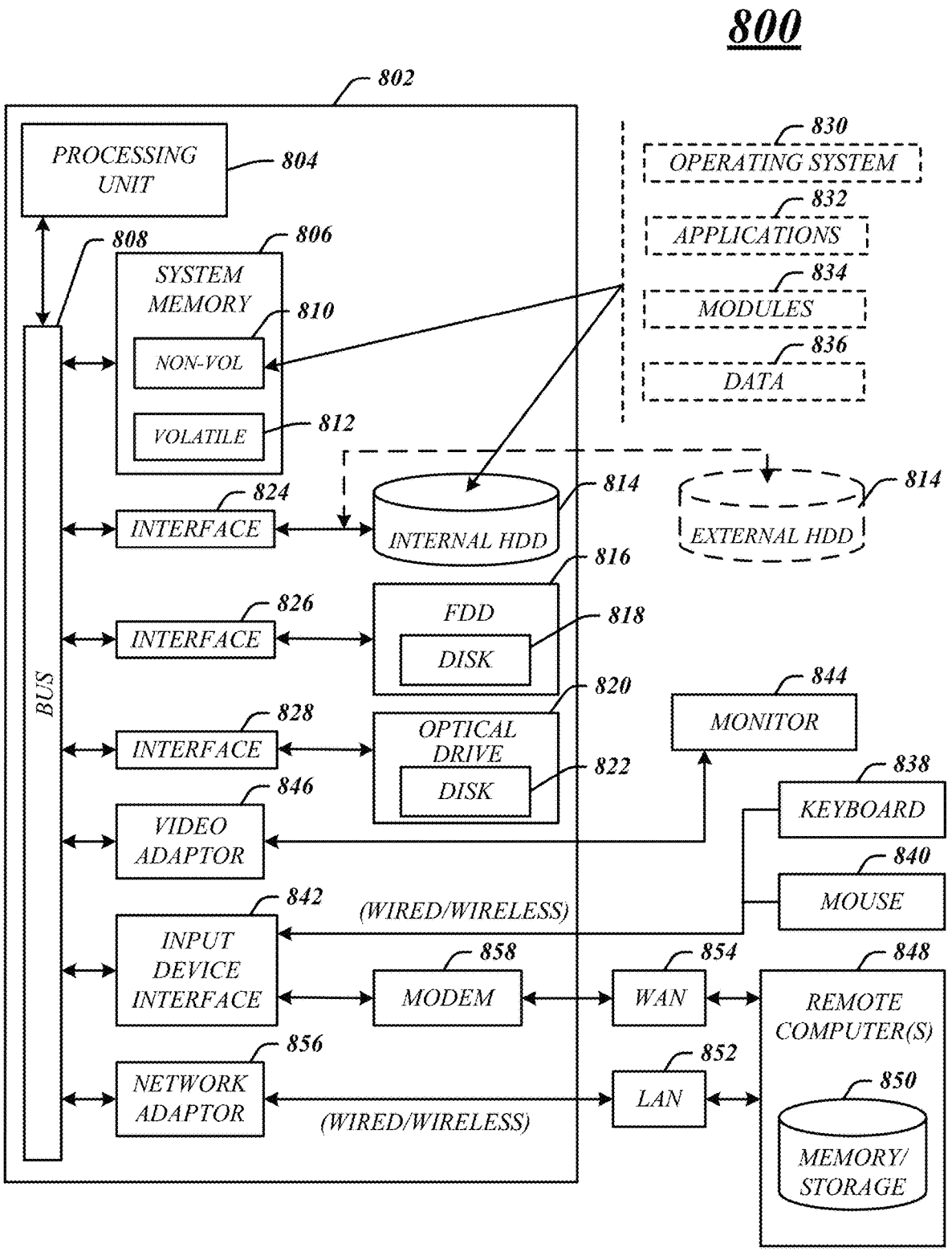
FIG. 8 illustrates an embodiment of a computing architecture according to the present disclosure.

FIG. 8 illustrates an embodiment of an exemplary computing architecture 800 suitable for implementing various embodiments as previously described. In various embodiments, the computing architecture 800 may comprise or be implemented as part of an electronic device. In some embodiments, the computing architecture 800 may be representative, for example, of computing device 802 and/or components thereof. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 800. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 800 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 800.

As shown in FIG. 8, the computing architecture 800 comprises a processing unit 804, a system memory 806 and a system bus 808. The processing unit 804 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 804.

The system bus 808 provides an interface for system components including, but not limited to, the system memory 806 to the processing unit 804. The system bus 808 can be any of several types of bus structure that may further interconnect to a memory bus (with or without a memory controller), a peripheral bus, and a local bus using any of a variety of commercially available bus architectures. Interface adapters may connect to the system bus 808 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 806 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 8, the system memory 806 can include non-volatile memory 810 and/or volatile memory 812. A basic input/output system (BIOS) can be stored in the non-volatile memory 810.

The computer 802 may include various types of computer-readable storage media in the form of one or more lower speed memory units, including an internal (or external) hard disk drive (HDD) 814, a magnetic floppy disk drive (FDD) 816 to read from or write to a removable magnetic disk 818, and an optical disk drive 820 to read from or write to a removable optical disk 822 (e.g., a CD-ROM or DVD). The HDD 814, FDD 816 and optical disk drive 820 can be connected to the system bus 808 by a HDD interface 824, an FDD interface 826 and an optical drive interface 828, respectively. The HDD interface 824 for external drive implementations can include at least one or both of Universal Serial Bus (USB) and IEEE 1384 interface technologies.

The drives and associated computer-readable media provide volatile and/or nonvolatile storage of data, data structures, computer-executable instructions, and so forth. For example, a number of program modules can be stored in the drives and memory units 810, 812, including an operating system 830, one or more application programs 832, other program modules 834, and program data 836. In one embodiment, the one or more application programs 832, other program modules 834, and program data 836 can include, for example, the various applications and/or components of computing device 48.

A user can enter commands and information into the computer 802 through one or more wire/wireless input devices, for example, a keyboard 838 and a pointing device, such as a mouse 840. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 804 through an input device interface 842 that is coupled to the system bus 808, but can be connected by other interfaces such as a parallel port, IEEE 884 serial port, a game port, a USB port, an IR interface, and so forth.

A monitor 844 or other type of display device is also connected to the system bus 808 via an interface, such as a video adaptor 846. The monitor 844 may be internal or external to the computer 802. In addition to the monitor 844, a computer typically includes other peripheral output devices, such as speakers, printers, and so forth.

The computer 802 may operate in a networked environment using logical connections via wire and/or wireless communications to one or more remote computers, such as a remote computer 848. The remote computer 848 can be a workstation, a server computer, a router, a personal computer, portable computer, microprocessor-based entertainment appliance, a peer device or other common network node, and typically includes many or all of the elements described relative to the computer 802, although, for purposes of brevity, only a memory/storage device 850 is illustrated. The logical connections depicted include wire/wireless connectivity to a local area network (LAN) 852 and/or larger networks, for example, a wide area network (WAN) 854. Such LAN and WAN networking environments are commonplace in offices and companies, and facilitate enterprise-wide computer networks, such as intranets, all of which may connect to a global communications network, for example, the Internet.

When used in a LAN networking environment, the computer 802 is connected to the LAN 852 through a wire and/or wireless communication network interface or adaptor 856. The adaptor 856 can facilitate wire and/or wireless communications to the LAN 852, which may also include a wireless access point disposed thereon for communicating with the wireless functionality of the adaptor 856.

When used in a WAN networking environment, the computer 802 can include a modem 858, or is connected to a communications server on the WAN 854, or has other means for establishing communications over the WAN 854, such as by way of the Internet. The modem 858, which can be internal or external and a wire and/or wireless device, connects to the system bus 808 via the input device interface 842. In a networked environment, program modules depicted relative to the computer 802, or portions thereof, can be stored in the remote memory/storage device 850. It will be appreciated that the network connections shown are exemplary and other means of establishing a communications link between the computers can be used.

The computer 802 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An apparatus, comprising:
   at least one processor;
   a memory coupled to the at least one processor, the memory comprising instructions that, when executed by the at least one processor, cause the at least one processor to:

train at least one machine learning quantitative structure-activity relationship (QSAR) model for modeling binding to an albumin target protein via:

building the at least one QSAR model using first known albumin binding data comprising data of a first set of compounds known to bind to albumin; and validating the at least one QSAR model using second known albumin binding data comprising data of a second set of compounds known to bind to albumin, the second set of compounds different from the first set of compounds;

wherein the at least one QSAR model is trained to receive candidate data as input, the candidate data comprising data of a set of candidate compounds with unknown binding affinity to albumin, the candidate data being different from the first known albumin binding data and the second known albumin binding data, wherein the at least one QSAR model is further trained to generate output comprising at least one potential compound with a binding affinity for binding to albumin, the at least one potential compound selected based on the at least one QSAR model from the set of candidate compounds;

generate an infusion profile for a patient based on the at least one potential compound; and cause an infusion pump of a dialysis machine to be controlled based on the infusion profile for the patient during a dialysis treatment of the patient.

2. The apparatus of claim 1, the instructions, when executed by the at least one processor, cause the at least one processor to train the at least one QSAR model to generate a prediction of a binding affinity value of the at least one potential compound.

3. The apparatus of claim 1, wherein the at least one QSAR model comprises at least one of a binding site I QSAR model trained to predict a binding affinity of a candidate for binding site I of albumin or a binding site II QSAR model trained to predict the binding affinity of a candidate for binding site II of albumin.

4. The apparatus of claim 3, wherein displacer compounds determined via the binding site I QSAR model have an indication of binding affinity of log K=log [% PPB/(101−% PPB)] and displacer compounds determined via the binding site II QSAR model have an indication of binding affinity of log K, wherein PPB refers to plasma protein binding.

5. The apparatus of claim 1, wherein the at least one QSAR model comprises at least one plasma protein binding (PPB) model.

6. The apparatus of claim 1, wherein the first known albumin binding data comprises data of compounds with a negative binding affinity to albumin and data of compounds with a positive binding affinity to albumin.

7. The apparatus of claim 1, wherein the set of candidate compounds are associated with displacer properties, wherein the displacer properties comprise at least one of the candidate compounds sharing a same binding site with the target protein, the candidate compounds having a binding affinity over a threshold value, the candidate compounds being associated with an approved dosage to provide displacement effects, the candidate compounds being applicable to a specified delivery process, the candidate compounds not requiring kidney excretion, or the candidate compounds being safe for a target patient population.

8. An apparatus, comprising:
at least one processor;
a memory coupled to the at least one processor, the memory comprising instructions that, when executed by the at least one processor, cause the at least one processor to:
access candidate data comprising data of a set of candidate compounds with unknown binding affinity to albumin, and
determine at least one potential compound with an affinity for binding to albumin from the candidate data by providing the candidate data as input to at least one machine learning quantitative structure-activity relationship (QSAR) model trained to model binding to an albumin target protein via:
building the at least one QSAR model using first known albumin binding data comprising data of a first set of compounds known to bind to albumin; and
validating the at least one QSAR model using second known albumin binding data comprising data of a second set of compounds known to bind to albumin, the second set of compounds different from the first set of compounds;
wherein the at least one QSAR model is trained to receive the candidate data as input, the candidate data different from the first known albumin binding data and the second known albumin binding data, to generate output comprising at least one potential compound with an affinity for binding to albumin, the at least one potential compound selected based on the at least one QSAR model from the set of candidate compounds;
generate an infusion profile for a patient based on the at least one potential compound; and
cause an infusion pump of a dialysis machine to be controlled based on the infusion profile for the patient during a dialysis treatment of the patient.

9. The apparatus of claim 8, the instructions, when executed by the at least one processor, to cause the at least one processor to train the at least one QSAR model to generate the output comprising a prediction of the binding affinity of the at least one potential compound.

10. The apparatus of claim 8, wherein the at least one QSAR model comprises at least one of a binding site I QSAR model trained to predict a binding affinity of a candidate for binding site I of albumin or a binding site II QSAR model trained to predict the binding affinity of a candidate for binding site II of albumin.

11. The apparatus of claim 10, wherein displacer compounds determined via the binding site I QSAR model have an indication of binding affinity of log K=log [% PPB/(101−% PPB)] and displacer compounds determined via the binding site II QSAR model have an indication of binding affinity of log K, wherein PPB refers to plasma protein binding.

12. The apparatus of claim 8, wherein the at least one QSAR model comprises at least one plasma protein binding (PPB) model.

13. The apparatus of claim 8, wherein the first known albumin binding data comprises data of compounds with a negative binding affinity to albumin and data of compounds with a positive binding affinity to albumin.

14. The apparatus of claim 8, wherein the set of candidate compounds are associated with displacer properties, wherein the displacer properties comprise at least one of the candidate compounds sharing a same binding site with the target protein, the candidate compounds having a binding affinity over a threshold value, the candidate compounds being associated with an approved dosage to provide displacement effects, the candidate compounds being applicable to a specified delivery process, the candidate compounds not requiring kidney excretion, or the candidate compounds being safe for a target patient population.

15. A method comprising:

training at least one machine learning quantitative structure-activity relationship (QSAR) model for modeling binding to an albumin target protein via:

building the at least one QSAR model using first known albumin binding data comprising data of a first set of compounds known to bind to albumin; and validating the at least one QSAR model using second known albumin binding data comprising data of a second set of compounds known to bind to albumin, the second set of compounds different from the first set of compounds;

wherein the at least one QSAR model is trained to receive candidate data as input, the candidate data comprising data of a set of candidate compounds with unknown binding affinity to albumin, the candidate data different from the first known albumin binding data and the second known albumin binding data, to generate output comprising at least one potential compound with an affinity for binding to albumin, wherein the at least one potential compound is selected based on the at least QSAR model from the set of candidate compounds; and administering a dialysis treatment using the at least one potential compound.

16. The method of claim 15, further comprising training the at least one QSAR model to generate a prediction of a binding affinity value of the at least one potential compound.

17. The method of claim 15, wherein the at least one QSAR model comprises at least one of a binding site I QSAR model trained to predict a binding affinity of a candidate for binding site I of albumin or a binding site II QSAR model trained to predict the binding affinity of a candidate for binding site II of albumin.

18. The method of claim 17, wherein displacer compounds determined via the binding site I QSAR model have an indication of binding affinity of $\log K = \log [\% \text{ PPB}/(101-\% \text{ PPB})]$ and displacer compounds determined via the binding site II QSAR model have an indication of binding affinity of $\log K$, wherein PPB refers to plasma protein binding.

19. The method of claim 15, wherein the at least one QSAR model comprises at least one plasma protein binding (PPB) model.

20. The method of claim 15, wherein the first known albumin binding data comprises data of compounds with a negative binding affinity to albumin and data of compounds with a positive binding affinity to albumin.

* * * * *